United States Patent
Wu et al.

(10) Patent No.: US 6,447,658 B1
(45) Date of Patent: Sep. 10, 2002

(54) LOW-DENSITY COATING FOR GAS SENSORS

(75) Inventors: Ming-Cheng Wu, Rochester Hills; Paul Kikuchi, Fenton; Kaplia Wadu-Mesthrige, Southfield, all of MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/739,548

(22) Filed: Dec. 15, 2000

(51) Int. Cl.$^7$ ................................................. B05D 3/02
(52) U.S. Cl. ................. 204/424; 204/431; 427/126.3; 427/126.4; 427/376.2; 427/385.5
(58) Field of Search .................... 427/126.3, 126.4, 427/376.2, 385.5; 204/424, 431

(56) References Cited

U.S. PATENT DOCUMENTS

| | | | |
|---|---|---|---|
| 5,178,744 A | * | 1/1993 | Nakazawa et al. ......... 204/425 |
| 5,290,595 A | * | 3/1994 | Fitch ........................ 427/244 |
| 5,409,650 A | * | 4/1995 | Holme ........................ 264/63 |
| 5,522,979 A | * | 6/1996 | Tatumoto et al. .......... 204/429 |
| 5,593,558 A | * | 1/1997 | Sugino et al. ............. 204/429 |

FOREIGN PATENT DOCUMENTS

| | | |
|---|---|---|
| EP | 0264338 | 4/1988 |
| EP | 0454924 | 11/1991 |
| EP | 0832865 | 4/1998 |
| JP | 56096240 | 8/1981 |
| JP | 57076448 | 5/1982 |
| WO | 0173418 | 10/2001 |

* cited by examiner

Primary Examiner—Michael Barr
(74) Attorney, Agent, or Firm—Vincent A. Cichosz

(57) ABSTRACT

A method for making a sensor is disclosed, comprising mixing a metal oxide with a polymer to create a composition. The composition is applied to at least a portion of the sensing element comprising two electrodes with an electrolyte disposed therebetween, and calcined to form a protective coating. A gas sensor created in accordance with the above-referenced method is also disclosed.

16 Claims, 2 Drawing Sheets

LOW-DENSITY COATING FOR GAS SENSORS

TECHNICAL FIELD

The present disclosure relates to gas sensors, and particularly a low-density coating for the sensing element.

BACKGROUND

The automotive industry has used exhaust gas sensors in automotive vehicles for many years to sense the composition of exhaust gases, namely, oxygen. For example, a sensor is used to determine the exhaust gas content for alteration and optimization of the air to fuel ratio for combustion.

One type of sensor uses an ionically conductive solid electrolyte between porous electrodes. For oxygen, solid electrolyte sensors are used to measure oxygen activity differences between an unknown gas sample and a known gas sample. In the use of a sensor for automotive exhaust, the unknown gas is exhaust and the known gas, (i. e. , reference gas), is usually atmospheric air because the oxygen content in air is relatively constant and readily accessible. This type of sensor is based on an electrochemical galvanic cell operating in a potentiometric mode to detect the relative amounts of oxygen present in an automobile engine's exhaust. When opposite surfaces of this galvanic cell are exposed to different oxygen partial pressures, an electromotive force ("emf") is developed between the electrodes according to the Nernst equation.

With the Nernst principle, chemical energy is converted into electromotive force. A gas sensor based upon this principle typically consists of an ionically conductive solid electrolyte material, a porous electrode with a porous protective overcoat exposed to exhaust gases ("exhaust gas electrode"), and a porous electrode exposed to a known gas's partial pressure ("reference electrode"). Sensors typically used in automotive applications use a yttria stabilized zirconia based electrochemical galvanic cell with porous platinum electrodes, operating in potentiometric mode, to detect the relative amounts of a particular gas, such as oxygen for example, that is present in an automobile engine's exhaust. Also, a typical sensor has a ceramic heater attached to help maintain the sensor's ionic conductivity at low exhaust temperatures. When opposite surfaces of the galvanic cell are exposed to different oxygen partial pressures, an electromotive force is developed between the electrodes on the opposite surfaces of the zirconia wall, according to the Nernst equation:

$$E = \left(\frac{-RT}{4F}\right)\ln\left(\frac{P_{O_2}^{ref}}{P_{O_2}}\right)$$

where:

E=electromotive force

R=universal gas constant

F=Faraday constant

T=absolute temperature of the gas $P_{O_2}^{ref}$ =oxygen partial pressure of the reference gas $P_{O_2}$=oxygen partial pressure of the exhaust gas Due to the large difference in oxygen partial pressure between fuel rich and fuel lean exhaust conditions, the electromotive force (emf) changes sharply at the stoichiometric point, giving rise to the characteristic switching behavior of these sensors. Consequently, these potentiometric oxygen sensors indicate qualitatively whether the engine is operating fuel-rich or fuel-lean, conditions without quantifying the actual air-to-fuel ratio of the exhaust mixture.

In a conventional sensor, the sensor comprises a first electrode capable of sensing an exhaust gas and a second electrode capable of sensing a reference gas with an ionically conductive solid electrolyte disposed therebetween. High temperatures and materials such as silicon, lead and the like, present in engine exhaust, can poison or otherwise damage the sensing electrode. In order to prevent poisoning/damage to the sensing electrode, a protective layer made of spinel or the like, has conventionally been applied to the sensing electrode.

The protective layer is designed to allow for the electrodes to sense the particular gas without inhibiting the performance of the sensor. A thick layer (or multiple layers) of protective coating more effectively inhibits the transmission of the poisoning materials, but at the expense of a decrease in the efficiency of the sensor. Furthermore, the protective layer itself can become clogged, inhibiting passage of exhaust gases for sensing. One conventional poison resistance technique comprises applying multiple layers of a heat resistant metal oxide to the electrode to form a protective layer. However, the multiple layers have a tendency to change the performance of the sensor and only provide limited poison protection.

Accordingly, there exists a need in the art for improved protective coatings for gas sensors.

SUMMARY

The drawbacks and disadvantages of the prior art are overcome by the low-density coating for a gas sensor and method for making the same. The method comprises mixing a metal oxide with a polymer to create a composition. The composition is applied to at least a portion of the sensing element comprising two electrodes with an electrolyte disposed therebetween, and calcined to form a protective coating. A gas sensor created according to the above-referenced method is also disclosed.

BRIEF DESCRIPTION OF THE DRAWINGS

Referring now to the figures, which are meant to be exemplary, not limiting, and wherein like elements are numbered alike in several figures.

DESCRIPTION OF THE PREFERRED EMBODIMENT

A protective coating for sensors, in particular oxygen sensors, is formed from a composition comprising a metal oxide and a fugitive material. Although described in connection with an oxygen sensor, it is to be understood that the protective coating can be employed with any type of sensor such as a nitrogen oxide sensor, hydrogen sensor, hydrocarbon sensor, or the like. Although described in connection with a planar sensor, it is to be understood that the protective coating can be employed with any type of sensor such as a conical, wide-range, and the like.

Figure 1:
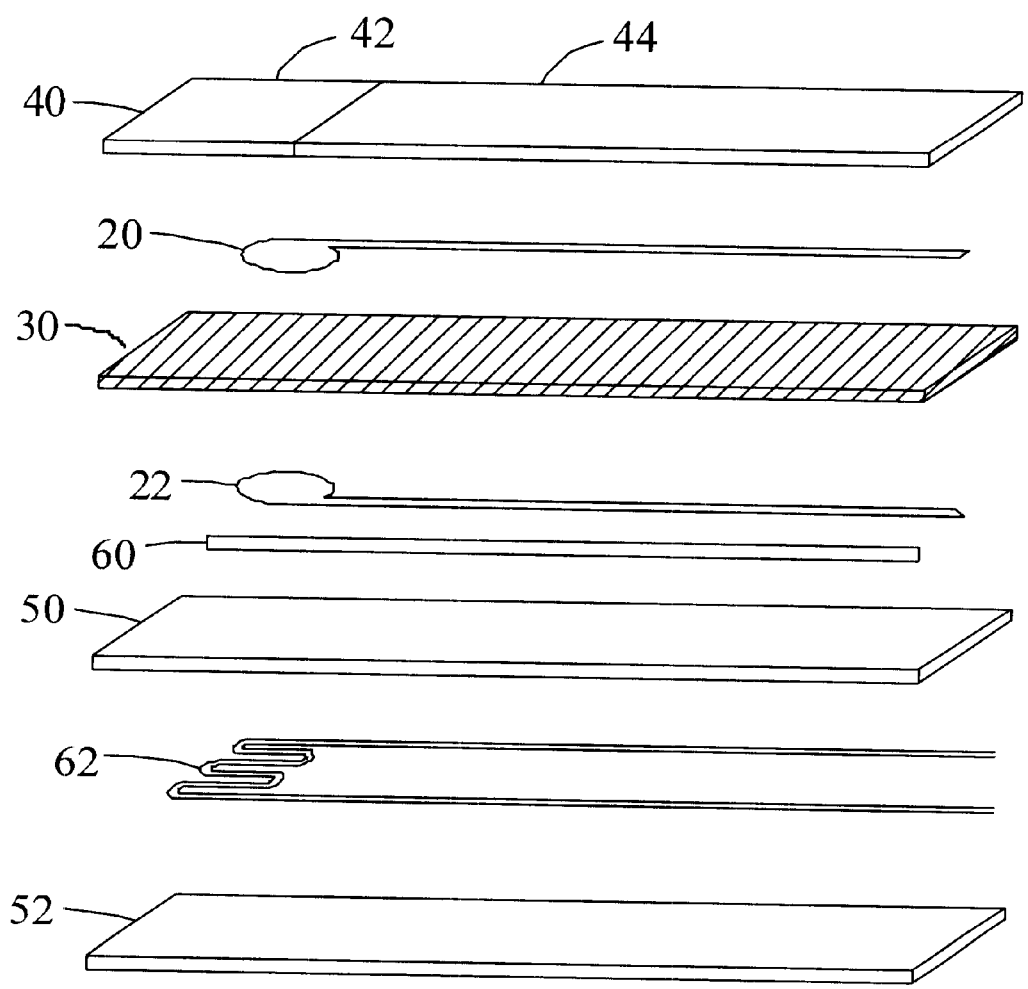
FIG. 1 is an expanded view of one embodiment of an oxygen sensor.

Referring to FIG. 1, the sensor element 10 is illustrated. The exhaust gas (or outer) electrode 20 and the reference gas (or inner) electrode 22 are disposed on opposite sides of, and adjacent to, a solid electrolyte layer 30 creating an electrochemical cell (20/30/22). On the side of the exhaust gas electrode 20 opposite solid electrolyte 30 is a protective insulating layer 40 having a dense section 44 and a porous section 42 that enables fluid communication between the exhaust gas electrode 20 and the exhaust gas. Meanwhile, disposed on the side of the reference electrode 22 opposites solid electrolyte 30 is a reference gas channel 60, which is in fluid communication with the reference electrode 22 and optionally with the ambient atmosphere and/or the exhaust gas. Disposed on a side of the reference gas channel 60 opposite the reference electrode 22 is a heater 62 for maintaining sensor element 10 at the desired operating temperature. Typically disposed between the reference gas channel 60 and the heater 62, as well as on a side of the heater opposite the reference gas channel 60, are one or more insulating layers 50, 52.

In addition to the above sensor components, conventional components can be employed, including but not limited to, lead gettering layer(s), leads, contact pads, ground plane(s), support layer(s), additional electrochemical cell(s), and the like. The leads (not shown), which supply current to the heater and electrodes, are typically formed on the same layer as the heater/electrode to which they are in electrical communication and extend from the heater/electrode to the terminal end of the gas sensor where they are in electrical communication with the corresponding via (not shown) and appropriate contact pads (not shown).

Insulating layers 50, 52, and protective layer 40, provide structural integrity (e.g., protect various portions of the gas sensor from abrasion and/or vibration, and the like, and provide physical strength to the sensor), and physically separate and electrically isolate various components. The insulating layer(s), which can be formed using ceramic tape casting methods or other methods such as plasma spray deposition techniques, screen printing, stenciling and others conventionally used in the art, can each be up to about 200 microns ($\mu$m) thick or so, with a thickness of about 50 $\mu$m to about 200 $\mu$m preferred. Since the materials employed in the manufacture of gas sensors preferably comprise substantially similar coefficients of thermal expansion, shrinkage characteristics, and chemical compatibility in order to minimize, if not eliminate, delamination and other processing problems, the particular material, alloy or mixture chosen for the insulating and protective layers is dependent upon the specific electrolyte employed. Typically these insulating layers comprise a dielectric material such as alumina, and the like.

Disposed between the insulating layers 50, 52, is a heater 62 that is employed to maintain the sensor element at the desired operating temperature. Heater 62 can be any conventional heater capable of maintaining the sensor end at a sufficient temperature to facilitate the various electrochemical reactions therein. The heater 62, which is typically platinum, aluminum, palladium, and the like, as well as mixtures, oxides, and alloys comprising at least one of the foregoing metals, or any other conventional heater, is generally screen printed or otherwise disposed onto a substrate to a thickness of about 5 $\mu$m to about 50 $\mu$m.

The heater maintains the electrochemical cell (electrodes 20, 22 and electrolyte 30) at a desired operating temperature. The electrolyte layer 30 can be solid or porous, can comprise the entire layer or a portion thereof, can be any material that is capable of permitting the electrochemical transfer of oxygen ions, should have an ionic/total conductivity ratio of approximately unity, and should be compatible with the environment in which the gas sensor will be utilized (e.g., up to about 1,000° C.). Possible electrolyte materials can comprise any material conventionally employed as sensor electrolytes, including, but not limited to, zirconia which may optionally be stabilized with calcium, barium, yttrium, magnesium, aluminum, lanthanum, cesium, gadolinium, and the like, as well as oxides, alloys, and combinations comprising at least one of the foregoing materials. For example, the electrolyte can be alumina and/or yttrium stabilized zirconia. Typically, the electrolyte, which can be formed via many conventional processes (e.g., die pressing, roll compaction, stenciling and screen printing, tape casting techniques, and the like), has a thickness of up to about 500 $\mu$m or so, with a thickness of about 25 $\mu$m to about 500 $\mu$m preferred, and a thickness of about 50 $\mu$m to about 200 $\mu$m especially preferred.

It should be noted that the electrolyte layer 30 and porous section 42 can comprise an entire layer or a portion thereof, e.g., they can form the layer, be attached to the layer (porous section/electrolyte abutting dielectric material), or disposed in an opening in the layer (porous section/electrolyte can be an insert in an opening in a dielectric material layer). The latter arrangement eliminates the use of excess electrolyte and protective material, and reduces the size of gas sensor by eliminating layers. Any shape can be used for the electrolyte and porous section, with the size and geometry of the various inserts, and therefore the corresponding openings, being dependent upon the desired size and geometry of the adjacent electrodes. It is preferred that the openings, inserts, and electrodes have a substantially compatible geometry such that sufficient exhaust gas access to the electrode(s) is enabled and sufficient ionic transfer through the electrolyte is established.

The electrodes 20, 22, are disposed in ionic contact with the electrolyte layer 30. Conventional electrodes can comprise any catalyst capable of ionizing oxygen, including, but not limited to, platinum, palladium, osmium, rhodium, iridium, gold, ruthenium, zirconium, yttrium, cerium, calcium, aluminum, silicon, and the like, and oxides, mixtures, and alloys comprising at least one of the foregoing catalysts. As with the electrolyte, the electrodes 20, 22 can be formed using conventional techniques. Some possible techniques include sputtering, painting, chemical vapor deposition, screen printing, and stenciling, among others. If a co-firing process is employed for the formation of the sensor, screen printing the electrodes onto appropriate tapes is preferred due to simplicity, economy, and compatibility with the co-fired process. Electrode leads and vias (not shown) in the insulating and/or electrolyte layers are typically formed simultaneously with electrodes.

An alternative sensor design can include a conical sensor. The conical sensor typically comprises an electrolyte body, having an inner surface, an outer surface, a cavity opening and a cavity terminus located at opposing ends of electrolyte body. An inner electrode is disposed on the inner surface, and an outer electrode is disposed on outer surface. The conical sensor can be formed in any generally cylindrical shape and is preferably tapered from the cavity opening to the cavity terminus. A protrusion is typically formed on the sensor element at a point between the cavity opening and the cavity terminus to define an upper shoulder and a lower shoulder that preferably extends completely around the circumference of a cross-section of electrolyte body. The protrusion is generally configured and dimensioned to engage a surface within a shell portion of the gas sensing apparatus into which the sensor element is received, thereby causing the inactive portion of the sensor, e. g. , the portion above and including the lower shoulder, to extend out of the shell portion while the active portion extends into the shell portion to contact the exhaust gas. The materials, as indicated above for the planar sensor, can also be utilized with the conical sensor.

Following the formation of the sensing element 10, a protective coating can be applied to the sensing element 10. This protective coating may optionally be used to coat the entire sensing element 10 or a portion of the sensing element 10. Conventional protective coatings are formed of a composition comprising a metal oxide and a fugitive material. Metal oxides having an affinity to filter out materials such as silica and zinc phosphate compounds, and other poisons, as well as having a high temperature stability (e. g. , up to about 900° C. or so), and preferably having a high surface area (e. g. , a surface area of about 50 m$^2$/g or greater, with about 100 m$^2$/g or greater preferred). Some possible metal oxides can include alumina, silica, and the like, and mixtures comprising at least one of the foregoing metal oxides. Conventional fugitive materials include carbon-based materials, such as carbon black. As used herein, a "fugitive material" means a material that will occupy space until the electrode is fired, thus leaving porosity in the coating.

Although protective coatings formed using carbon black are suitable, they fail to obtain a desired density. Essentially, carbon black particles have a size of about 0. 02 $\mu$m to about 0. 2 $\mu$m. Aggregates, which may be as large as 1. 0 $\mu$m typically break during coating preparation.

In contrast, when a polymer is employed as the fugitive material, greater non-breakable particle size range is available. A suitable polymer can e a polymer material including, but not limited to, polystyrene, poly(methylmethacrylate), polystyrene-divinylbenzene, and the like, and combinations comprising at least one of the foregoing materials. The average size of the polymer particles can be up to about 100 $\mu$m, with about 0. 2 $\mu$m to about 50 $\mu$m preferred, about 0.5$\mu$m to about 10 $\mu$m more preferred, and about 0.5$\mu$m to about 5 $\mu$m especially preferred. Most preferably, the polymer comprises a range of particle sizes of about 0. 2 $\mu$m to about 100 $\mu$m.

When forming the protective coating, the metal oxide component is preferably prepared by forming a slurry. The metal oxide component of the protective coating can be prepared by mixing a coarse (e. g. , about 30 $\mu$m or greater in diameter, with about 30 $\mu$m to about 50 $\mu$m in diameter, preferred), high-surface area (e. g. , about 100 m$^2$/g or greater) alumina, such as theta-alumina ($\theta$-Al$_2$O$_3$), lanthanum oxide (La$_2$O$_3$) stabilized $\theta$-Al$_2$O$_3$, strontium oxide stabilized alumina, barium oxide stabilized alumina, with a fine (e. g. , about 10 $\mu$m or less in diameter, with about 0.5$\mu$m or less in diameter preferred) alpha alumina ($\alpha$-Al$_2$O$_3$) and a binder, such as aluminum nitrate (Al(NO$_3$)$_3$) to form a base slurry. The slurry can comprise about 45 weight percent (wt. %) to about 49 wt. % of $\theta$-Al$_2$O$_3$, about 45 wt. % to about 49 wt. % of /$\alpha$-Al$_2$O$_3$, and about 2 wt. % to about 10 wt. % of Al(NO$_3$)$_3$. In another embodiment, a slurry can be formed of La$_2$O$_3$ stabilized alumina with about 47 wt. % of La$_2$O$_3$ stabilized $\theta$-Al$_2$O$_3$, about 47 wt. % of $\alpha$-Al$_2$O$_3$, and about 6 wt. % of Al(NO$_3$)$_3$. The percentage of solids in the slurry is about 45 wt. % to about 55 wt. %, with about 48 wt. % to about 52 wt. % preferred. The slurry is stirred thoroughly prior to being milled (e. g. , using a vibro-energy grinding mill) for about 2 hours, or so, to break down the aggregates of $\theta$-Al$_2$O$_3$. During milling, the size of the $\theta$-Al$_2$O$_3$ aggregates (d$_{50}$) decrease to less than about 5 $\mu$m.

Following the milling of this slurry, about 25 wt. % to about 40 wt. %, with about 30 wt. % to about 35 wt. % preferred, of the total solids of coarse La$_2$O$_3$ stabilized $\theta$-Al$_2$O$_3$ is mixed into the base slurry. The polymer is then added to the slurry. About 3 wt. % to about 15 wt. %, with about 5 wt. % to 10 wt. % preferred, is added to the base slurry to obtain a low-density "fluffy" alumina slurry.

The slurry can then applied as a protective coating to at least a portion of the sensing element. The sensing element is immersed in the slurry, which is preferably stirred at a constant speed and then withdrawn from the slurry. The amount of coating deposited on the sensing element depends upon the physical and chemical properties of the slurry, such as viscosity and pH, as well as the withdrawal rate. For example, using a conical oxygen sensor element, about 150 milligrams (mg) to about 350 mg of protective coating adhered to the element (via wet pickup) by manipulating the withdrawal rate. The protective coating created was uniform and crack-free. About 200 mg to about 300 mg of wet pickup (or about 120 mg to about 190 mg of calcined pickup) is preferred.

Following the depositing of the coating on the sensing element, it is optionally dried at temperatures up to about 100° C. Next, the element can be calcined at a temperature sufficient to burn off the fugitive material, such as about 500° C. for about 2 hours, prior to assembly into the sensor.

As with the pore size and porosity, the thickness of the protective coating is based upon the ability to filter out poisoning particulates while allowing passage of the exhaust gases to be sensed. Although a multi-layered coating can be employed, the protective coating is preferably a single layer having an overall thickness of up to about 300 $\mu$m, with a thickness of about 100 $\mu$m to about 200 $\mu$m preferred, and with a thickness of about 150 $\mu$m to about 200 $\mu$m also preferred.

Figure 2:
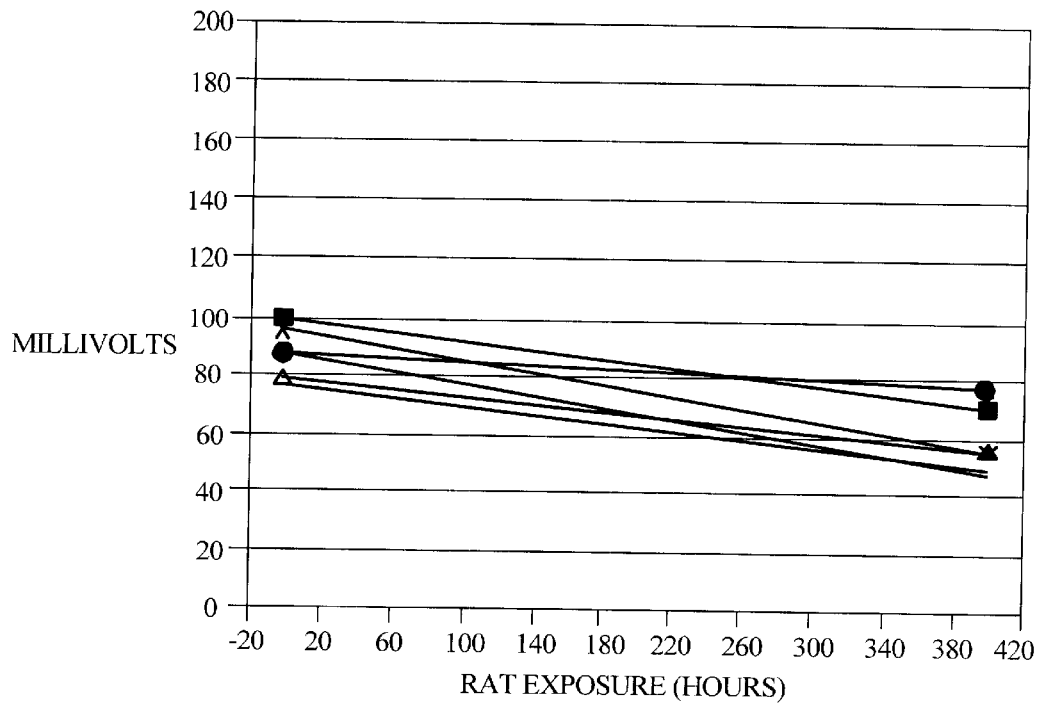
FIG. 2 is graph showing a severe zinc-phosphorous poisoning rapid aging test (RAT) for various sensors with hours of RAT exposure time on the X axis (hours) and lean voltage on the Y axis in millivolts (mv).
Figure 3:
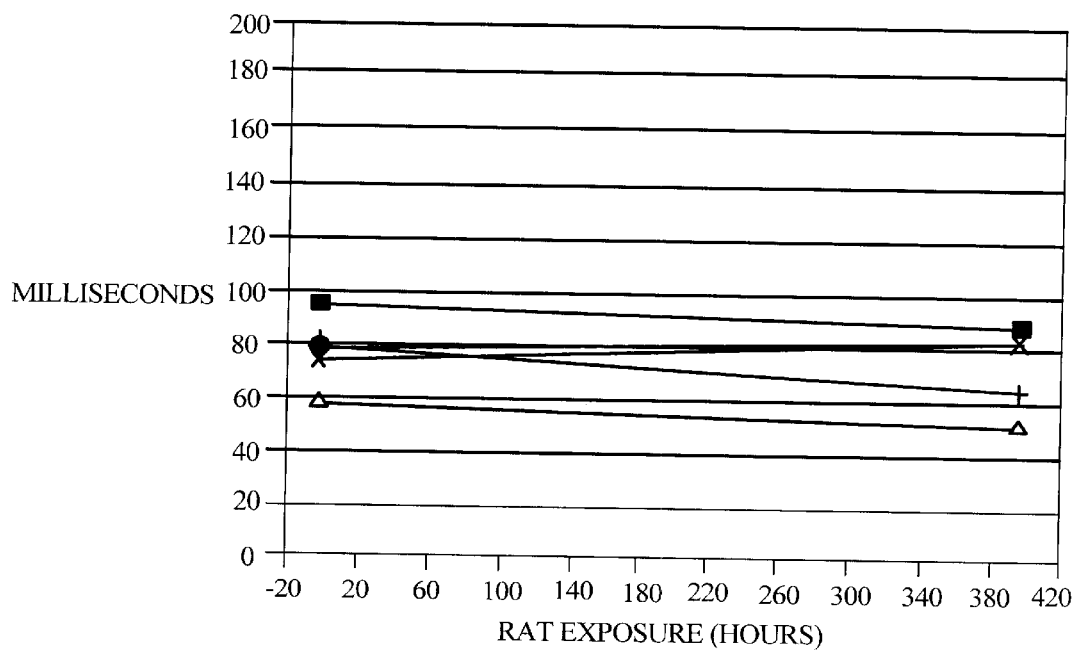
FIG. 3 is a graph showing a severe RAT test for various sensors with hours of RAT exposure time on the X axis (hours) and rich to lean response time on the Y axis in milliseconds (ms).

An experiment was completed with an oxygen sensor, having a low-density coating, in a working engine. In this experiment, a low-density alumina coating was prepared using unmilled, coarse alumina and a fugitive polymer. The monodispersed polystyrene was used as the fugitive material that has a particle size of about 0.5m. The sensor was subjected to a 400-hour severe zinc-phosphorous poisoning rapid aging test (RAT), which simulates 200,000 miles of vehicle age. FIGS. 2 and 3 illustrate engine performance data of lean voltage and rich-to-lean transition time, respectively. The results indicate that all of the oxygen sensor parts coated with the low-density coating, formed from a composition having about 5 wt. % to about 12 wt. % of a polymer, passed 400 hours of severe RAT poisoning without noticeable performance degradation. However, engine performance data from the oxygen sensors parts having carbon black formed similar low-density alumina coatings exhibited performance degradation after a 400-hour RAT durability test.

The use of a polymer as a fugitive material produces a low-density coating which inhibits the formation of glass that covers coating surfaces after prolonged exposure to engine exhaust. The polymer provides a consistent low-density alumina coating, has a greater particle size range than conventional fugitive materials, is chemically stable, and is physically non-breakable in slurry preparation.

While preferred embodiments have been shown and described, various modifications and substitutions may be made thereto without departing from the spirit and scope of the invention. Accordingly, it is to be understood that the apparatus and method have been described by way of illustration only, and such illustrations and embodiments as have been disclosed herein are not to be construed as limiting to the claims.

What is claimed is:

1. A method for making a sensor, comprising;
   mixing a metal oxide with a polymer to create a composition;
   applying said composition to at least a portion of a sensing element comprising two electrodes with an electrolyte disposed therebetween; and
   calcining said sensing element;
   wherein said metal oxide has a surface area of about 50 $m^2/g$ or greater.

2. The method of claim 1, wherein said metal oxide has a temperature stability of up to about 900° C.

3. The method of claim 2, wherein said metal oxide is selected from the group consisting of alumina, silica, and mixtures comprising at least one of the foregoing metal oxides.

4. The method of claim 3, wherein said alumina is selected from the group consisting of theta-alumina, alpha-alumina, lanthanum oxide stabilized theta-alumina, strontium oxide stabilized alumina, barium oxide stabilized alumina, and combinations comprising at least one of the foregoing metal oxides.

5. The method of claim 1, wherein said polymer is a material selected from the group consisting of polystyrenes, polymethylmethacrylates, polystyrene-divinylbenzenes and combinations comprising at least one of the foregoing polymers.

6. The method of claim 1, wherein said polymer has a particle size of about 0.2 $\mu$m to about 100 $\mu$m.

7. The method of claim 6, wherein said polymer has a particle size of about 0.5 $\mu$m to about 10 $\mu$m.

8. The method of claim 1, wherein said polymer has a range of particle sizes from about 0.2 $\mu$m to about 100 $\mu$m.

9. The method of claim 1, wherein said composition comprises about 3 wt. % to about 15 wt. % of said polymer.

10. The method of claim 9, wherein said composition comprises about 5 wt. % to about 10 wt. % of said polymer.

11. A gas sensor created according to the method of claim 1.

12. The method of claim 1, wherein calcining said sensing element produces a protective coating on said sensing element.

13. The method of claim 3, wherein said metal oxide comprises silica.

14. The method of claim 4, wherein said alumina is selected from the group consisting of theta-alumina, lanthanum oxide stabilized theta-alumina, strontium oxide stabilized alumina, barium oxide stabilized alumina, and combinations comprising at least one of the foregoing aluminas.

15. The method of claim 12, wherein said protective coating has a thickness of up to about 300 $\mu$m.

16. The method of claim 12, wherein said protective coating has a thickness of up to about 100 $\mu$m to about 200 $\mu$m.

* * * * *